United States Patent
Clarke et al.

(10) Patent No.: US 7,124,996 B2
(45) Date of Patent: Oct. 24, 2006

(54) AUTOMATIC CLAMP APPARATUS FOR IV INFUSION SETS USED IN PUMP DEVICES

(75) Inventors: Christopher J. Clarke, Basingstoke (GB); René Rüedi, Farnborough (GB)

(73) Assignee: Cardinal Health 303, Inc., San Diego, CA (US)

( * ) Notice: Subject to any disclaimer, the term of this patent is extended or adjusted under 35 U.S.C. 154(b) by 0 days.

(21) Appl. No.: 10/892,941

(22) Filed: Jul. 16, 2004

(65) Prior Publication Data

US 2006/0011873 A1  Jan. 19, 2006

(51) Int. Cl.
*F16K 7/04* (2006.01)

(52) U.S. Cl. .......................... 251/7; 251/105; 604/250

(58) Field of Classification Search .................. 251/4, 251/7, 105; 604/246, 249, 250, 256
See application file for complete search history.

(56) References Cited

U.S. PATENT DOCUMENTS

| | | | |
|---|---|---|---|
| 2,889,848 A * | 6/1959 | Redmer .................. | 137/315.07 |
| 4,398,542 A | 8/1983 | Cunningham et al. | |
| 4,404,440 A | 9/1983 | Busche et al. | |
| 5,437,635 A | 8/1995 | Fields et al. | |
| D362,062 S | 9/1995 | Botts et al. | |
| 5,453,098 A | 9/1995 | Botts et al. | |
| 5,967,484 A | 10/1999 | Morris et al. | |
| 6,354,279 B1 | 3/2002 | Gaston et al. | |
| 6,629,955 B1 | 10/2003 | Morris et al. | |
| 2002/0165503 A1 | 11/2002 | Morris et al. | |

* cited by examiner

*Primary Examiner*—Edward K. Look
*Assistant Examiner*—John K. Fristoe, Jr.
(74) *Attorney, Agent, or Firm*—Fulwider Patton LLP (57) ABSTRACT

A clamp apparatus for selectively occluding a resilient tube to prevent free flow of fluid in the tube. The device comprises a base member to which the resilient IV tube is attached or through which it passes, and a slide clamp that slides relative to the base member and relative to the tube. The aperture in the slide clamp has a relatively open hole at one end, through which the tube passes when the slide clamp is an open position, allowing fluid to flow through the tube. The aperture also has a relatively constricted slot at the other end, through which the tube passes when the slide clamp is in the occluding position, preventing fluid flow through the tube. A deflectable cantilevered locking arm on the base interlocks with a detent on the slide clamp to lock the slide clamp at the occluding position to avoid inadvertent free flow. A release tab that is used to release the locking arm from the slide clamp is located off center to avoid inadvertent activation. The deflectable arm is unstressed when the slide clamp is in either the occluding or the open positions. A stop device prevents over-stressing the release tab when it is moved. In one embodiment, the clamp apparatus may be slid along the IV tube to a desired location.

20 Claims, 10 Drawing Sheets

AUTOMATIC CLAMP APPARATUS FOR IV INFUSION SETS USED IN PUMP DEVICES

FIELD OF INVENTION

The invention is generally related to clamps used on flexible IV tubing in the field of intravenous (IV) infusion devices such as peristaltic pumps, and more particularly, to clamping devices used to prevent the free flow of fluids through an IV tube when the infusion pump is disengaged from the IV tube.

BACKGROUND OF THE INVENTION

It is a common practice to deliver fluids such as medications to a patient intravenously by means of a pumping device, such as a peristaltic pump. Such pumps are useful because they can deliver the medication in a highly controlled and precise fashion, and because they do so without coming in contact with the medication. The fluid is moved through a flexible IV tube by pressing a pumping member against the tube sufficiently to move the fluid in the tube downstream towards the patient. In the case of peristaltic mechanisms having multiple pumping fingers, the fingers are moved against the tube in a sequential manner from upstream to downstream to sequentially occlude the tube thereby moving the fluid in the tube downstream towards the patient. When the IV tube is mounted correctly in the pump, the IV tube is at all times occluded by one of the pumping members, thereby preventing the "free flow" of fluid to the patient. "Free flow" of medical fluids is undesirable since the flow of the fluid is uncontrolled and the prescribed treatment is not followed.

It is common for the peristaltic pumping mechanism to be located in a housing with a hinged door. The tube through which the fluid is to be moved is placed in contact with the pumping mechanism inside the door, with the ends of the tubing typically extending out the top and bottom of the door opening. As the door is shut over the tube, a platen on the inside of the door presses against the IV tube to provide a backing surface against which the pumping members can occlude the tube. The platen is typically spring loaded, although not always, against the pumping mechanism so that one or more of the pumping fingers of the pumping mechanism occludes the tube once the door is shut over the tube. This then prevents free flow while the door is shut.

This arrangement of the IV tube relative to the pumping mechanism requires that there be some means for preventing flow in the tube when the door of the pump is open. Merely opening the pump door would relieve the tube from the occluding pumping mechanism/platen combination and free flow could possibly occur. This could result in the uncontrolled infusion of medication into the patient under the influence of the static head pressure in the tube, or blood from the patient could flow back into the IV tube. Known devices for preventing the unwanted flow in the tube include manual clamps on the tube separate from the infusion pump, and automatic occluding devices mounted on the pump. The manual devices require some manipulation skill on the part of the attending technician, and there is always the chance that the technician will forget to properly time the manual clamping process of the tube before the door of the pump is opened. Furthermore, the door may be accidentally opened, resulting in free flow in the tube.

Automatic devices mounted on the infusion pump for assisting in clamping and unclamping infusion tubes have improved. In particular, the reliability in timing the occlusion and release (unocclusion) of the tube with the disengagement and engagement, respectively, of tube with the pumping members has improved. Typically, the action of opening the door is relied upon to initiate the occlusion of the IV tube by a clamp, and the action of closing the door is relied upon to initiate the release or unocclusion of the tube by an IV tube clamp. However, there still can occur the possibility of an inadvertent free flow of fluid through the IV tube due to operator error in regard to use of such devices.

Hence, those skilled in the art have identified a continuing need to provide an improved apparatus that will automatically and positively occlude an IV tube before the occluding pumping mechanism is disengaged from the tube. A further need has been recognized for an apparatus that will automatically and positively maintain the IV tube in an occluded state until after the occluding pumping mechanism is engaged with the tube. A still further need has been recognized for an apparatus that will reliably occlude the IV tube, that is inexpensive to manufacture, and is easy to use. Yet a further need has been recognized for an apparatus that can be manually operated between occluding and nonoccluding configurations. The present invention fulfills these needs and others.

SUMMARY OF THE INVENTION

Briefly and in general terms, the present invention is directed to a clamp apparatus for selectively preventing fluid flow through a resilient tube and comprises a base having a tube aperture at which the resilient tube may be located, the base having a longitudinal center line, a slide clamp slidably mountable on the base for movement between an occluding position and an open position, the slide clamp having a longitudinal center line, a clamp aperture formed in the slide clamp for receiving the tube therethrough, a constricted region formed in the clamp aperture, the constricted region occluding the tube to prevent fluid flow through the tube when the slide clamp is in the occluding position, an open region formed in the clamp aperture, the open region allowing fluid flow through the tube when the slide clamp is in the open position, a locking component formed on the slide clamp, and a flexible cantilevered locking arm mounted on the base, the locking arm having a release tab formed thereon but located at a position offset from the longitudinal center line of the base, the locking arm being biased toward a locking position wherein the locking arm engages the locking component of the slide clamp to prevent movement of the slide clamp from the occluding position to the open position, and the release tab being movable to deflect the locking arm wherein the locking arm is disengaged from the locking component to allow subsequent movement of the slide clamp from the occluding position to the open position.

In accordance with another aspect of the invention, the tube aperture of the base slidably receives the resilient tube such that the base may be slid along the tube to a selected position when the slide clamp is in the open position.

In other aspects of the invention, the locking arm further comprises a release tab for releasing the flexible arm from the slide clamp, to allow subsequent movement of the slide clamp from the occluding position to the open position. Further, the base comprises a stop surface located at a position adjacent the release tab to interfere with movement of the release tab beyond a preselected range of movement. The slide clamp comprises a detent into which the locking arm is biased and located when the slide clamp is in the occluding position, the detent being large enough to receive the locking arm without contact while the slide clamp is in the occluding position whereby the locking arm is under no stress. The slide clamp further comprises a ramp to receive the locking arm when the slide clamp is in the open position, the ramp formed to be deeper than the arm whereby the arm is not under stress when the slide clamp is in the flow position. The ramp is formed to guide the locking arm into a detent formed in the slide clamp as the slide clamp is being moved from the open position to the occluding position to thereby lock the slide clamp in the occluding position.

In yet other aspects, the aperture of the slide clamp is approximately tear-drop shaped, the constricted region comprises an elongated slot portion, the flow region comprises a rounded portion, the tube is located in the slot portion when the slide clamp is in the occluding position, and the tube is located in the round portion when the slide clamp is in the open position.

In additional detailed features, the tube aperture comprises a tube sleeve within which a resilient tube end may be permanently mounted. The tube aperture comprises a fluid passageway through the base, whereby the resilient tube is connected in fluid communication with the passageway. Further, the clamp apparatus comprises a pressure interface device located in line with the resilient tube, the pressure interface device having a pressure membrane mounted in a housing, the pressure membrane formed to conduct pressure increases and decreases of the resilient tubing to a pressure sensor located in a medical instrument.

In further aspects in accordance with the invention, the slide clamp further comprises a front pushing flange large enough to receive a digit of an operator used to push the clamp apparatus into position in a medical infusion pump, the pushing surface being concave. The release tab of the locking arm is located at a position other than behind the pushing flange. In a much more detailed aspect, the release tab is located at a sideways position in relation to the pushing flange. Additionally, the base comprises a rounded mounting end whereby pressing the clamp into operative position in an infusion pump is facilitated.

The novel features of this invention, as well as the invention itself, both as to its structure and its operation, will be best understood from the accompanying drawings, taken in conjunction with the accompanying description.

DESCRIPTION OF PREFERRED EMBODIMENTS

Figure 1:
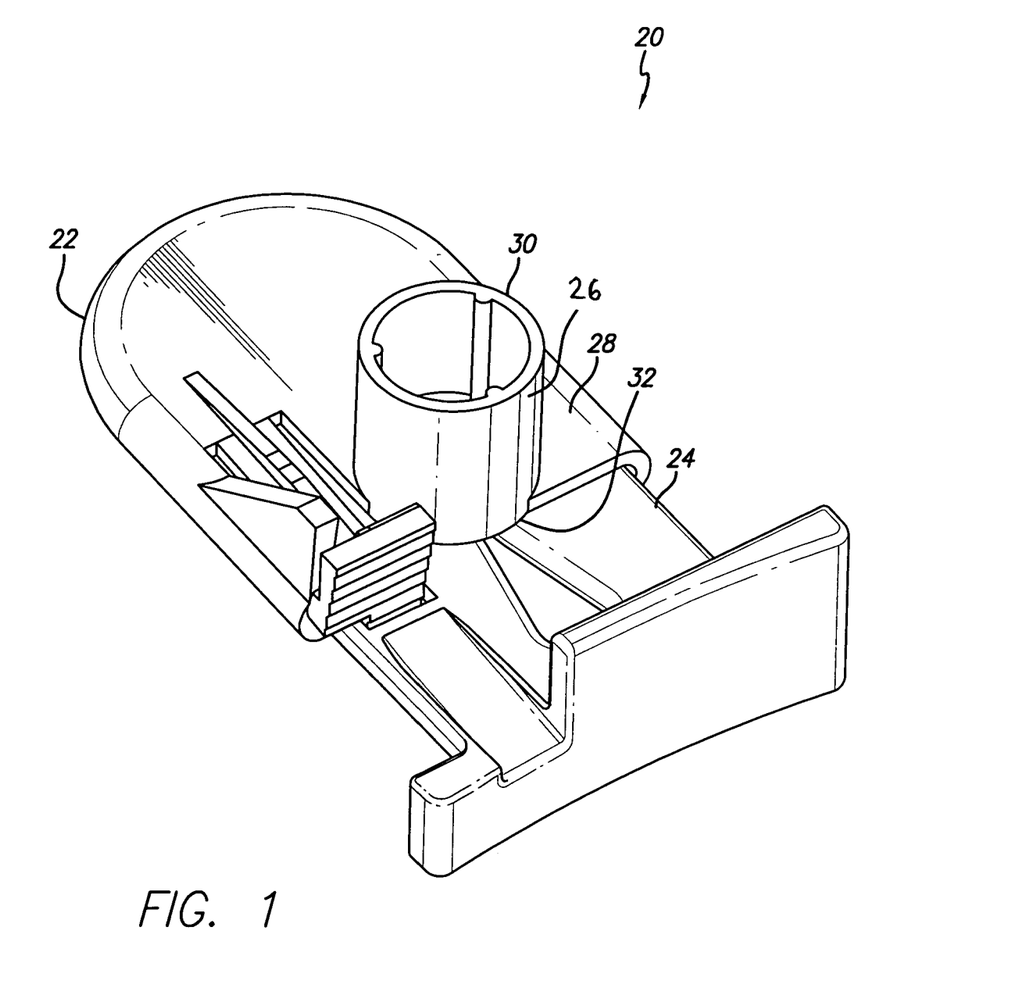
FIG. 1 is a perspective view of the automatic clamp apparatus in accordance with aspects of the present invention showing the slide clamp in the occlusion position at which it is partially withdrawn from the base.

Referring now to the drawings with more particularity, in which like reference numerals refer to like or corresponding elements among the several views, FIG. 1 presents an automatic clamp apparatus 20 for intravenous (herein referred to as "IV") infusion sets used in pump devices. The clamp apparatus 20 comprises generally a relatively open, box shaped base or frame 22 and a mating slide clamp 24. Both parts can be formed by injection molding from various plastic materials. The solid body of the slide clamp 24 is shaped and sized to slide within the base 22. In the embodiment shown, the base 22 has a tower 26 formed on the top surface 28 of the base, with the tower extending upwardly from the base and substantially perpendicular to the base. The top end 30 of the tower 26 is formed as a female tube connector into which a resilient IV tube can be attached. A pumping tube or other type of fluid conduit can be attached to the base by other means if desired. The open bottom end 32 of the tower is attached to the base and it is also formed as a female tube connector into which an IV tube or other conduit can be attached. The IV tube and the pumping tube can be the same tube if desired, simply threading the IV tube through the tower, through the base, and through the slide clamp such that the automatic clamp apparatus 20 can be slid along the IV tube to a desired location.

Figure 2:
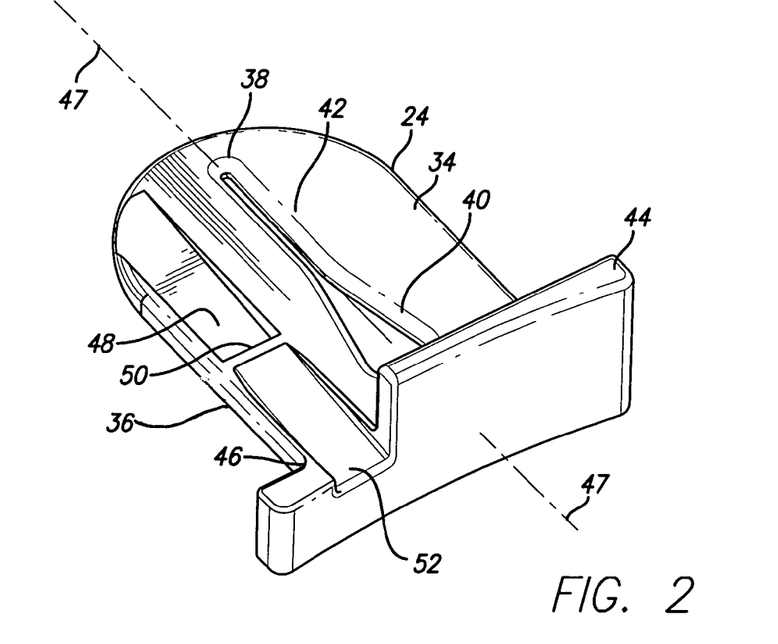
FIG. 2 is a front left-side perspective view of the slide clamp shown in FIG. 1 showing the aperture, the detent, the ramp, and the pushing flange.

Referring now also to FIG. 2, the slide clamp 24 is penetrated from its top surface 34 to its bottom surface 36 by an elongated aperture 38. The elongated dimension of the aperture 38 is arranged on the slide clamp to be parallel to the direction of the relative sliding movement between the base 22 and the slide clamp 24. The aperture 38 of the slide clamp comprises an open portion 40 and an occluding portion 42. The open portion is large enough so that a tube received by the open portion would not be occluded whereas the occluding portion is small enough so that it would occlude a received tube. The width of the slot of the occluding portion is sufficiently small that a selected IV tube passing through the slot would be completely occluded and would remain occluded against a foreseeable range of fluid pressures in the IV tube. The range of pressure against which the tube would remain occluded would include at least the static head anticipated during normal use of the infusion apparatus.

The slide clamp 24 also includes a pushing flange 44 at its front edge 46. The pushing flange is somewhat concave, although the "concave" surface may not necessarily be curved; it may in fact have converging straight surfaces or surfaces of other shapes. The purpose of the pushing flange is to guide the digit of an operator to the approximate center of the slide clamp for the purpose of mounting the entire automatic clamp apparatus 20 (FIG. 1) into an infusion pump. Such an operation may be seen by reference to U.S. Pat. No. 6,629,955 to Morris, particularly FIG. 10. U.S. Pat. No. 6,629,955 to Morris is incorporated herein by reference. Guiding the digit of an operator to the center of the pushing flange is more likely to result in the application of centerline force on the automatic clamp apparatus and thereby to result in the correct mounting of the clamp apparatus in the pump. For convenience, the shape of the pushing surface of the pushing flange 44 is referred to as "concave" although the surfaces may be other than curved, as discussed above. It will be noted that in this embodiment, the aperture 38 is also located on the longitudinal centerline 47 of the slide clamp.

Also shown in FIG. 2 is a locking detent 48 having a locking detent edge 50. The particular operation of the detent will be shown later but its purpose is to prevent movement of the slide clamp from the occluding position to the open position in the base without intended action. Further shown is a ramp 52 at the front of the slide clamp for receiving a locking arm of the base when the slide clamp is in the open position.

Figure 3:
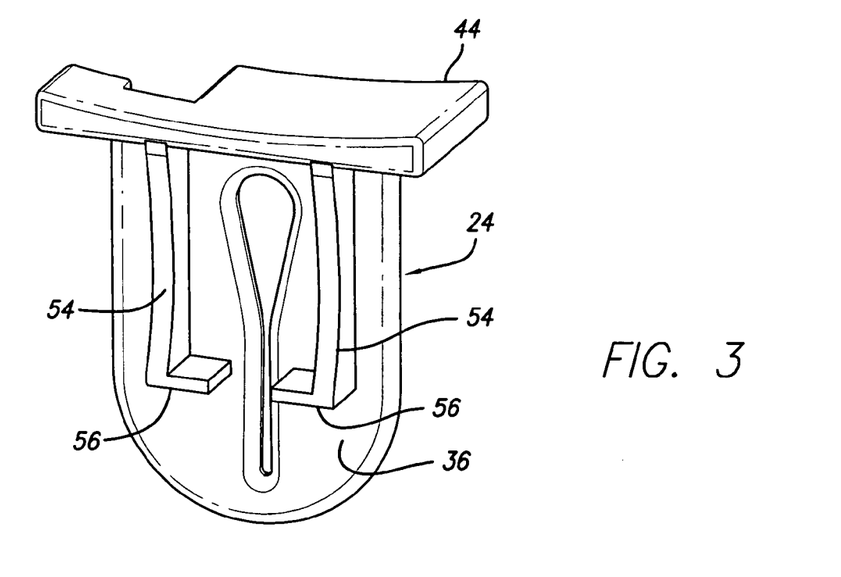
FIG. 3 is a bottom right-side perspective view of the slide clamp shown in FIG. 1 showing the aperture, the pushing flange, and the pulling projections.
Figure 4:
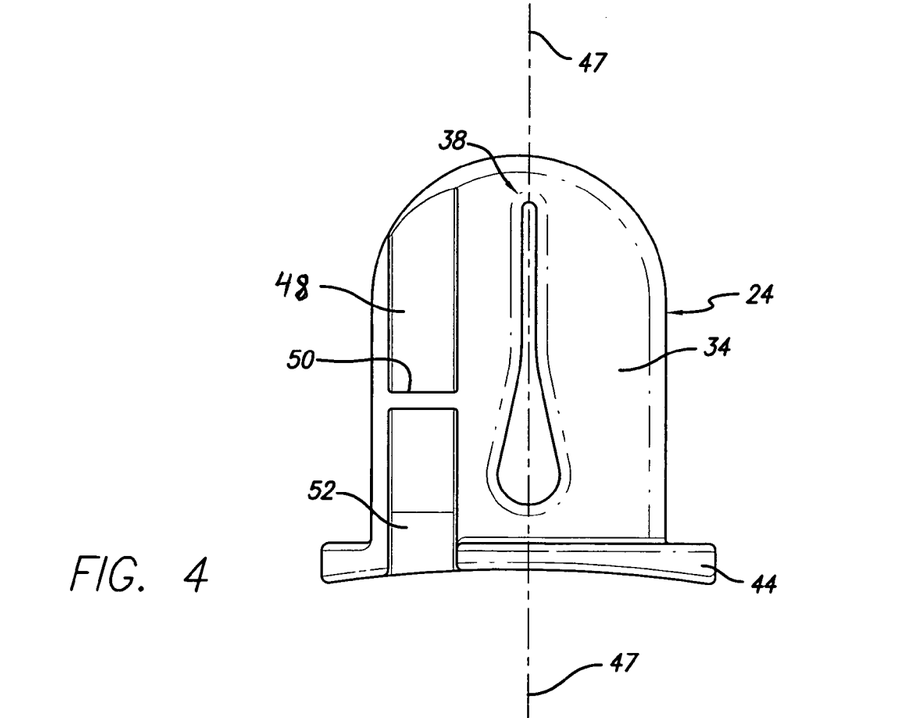
FIG. 4 is a top plan view of the slide clamp of FIGS. 1 through 3.
Figure 5:
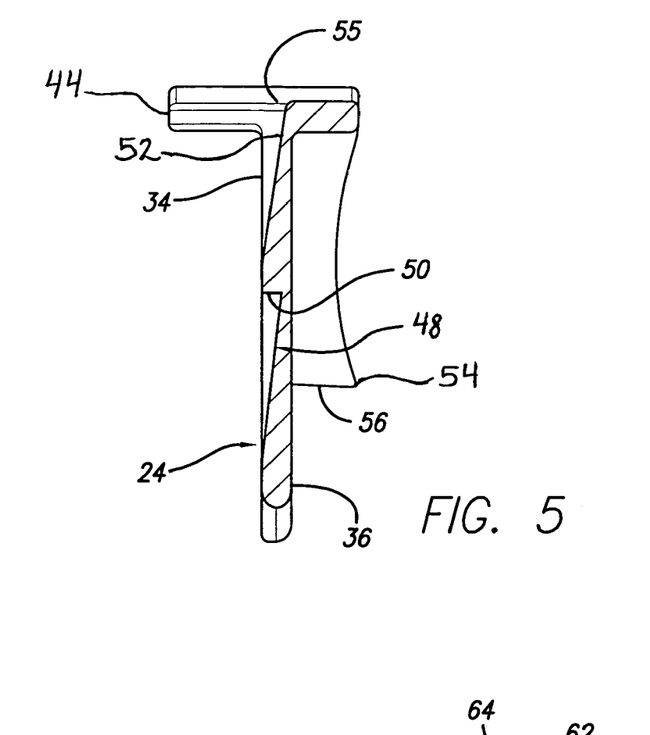
FIG. 5 is a left side, partially cutaway view of the slide clamp of FIGS. 1 through 4 showing a pulling projection, the detent, and the ramp.

Referring now to the perspective view of FIG. 3 and the views of FIGS. 4 and 5, the bottom surface 36 of the slide clamp 24 includes pulling projections 30 that project downwardly from the bottom surface presenting a substantially vertical pulling face 56 to engage the latch on the door of the pump housing (not shown) to withdraw the slide clamp 24 partially out of engagement with the base 22 before the door is opened. Pulling or withdrawing the slide clamp partially out of the base moves the slide clamp from its open position to its occluding position (FIG. 1). The pushing flange 44 of the slide clamp also presents a substantially vertical pushing face against which the door of the pump or some other device pushes to fully insert the slide clamp into the base when the door of the pump is closing or after it has been closed. Pushing the slide clamp into full insertion with the base moves the slide clamp from its occluding position to its open position. Also shown in FIGS. 4 and 5 are the detent 48 and the ramp 52. Both are formed in the material of the slide clamp and the depth of both can be best seen from FIG. 5.

Figure 6:
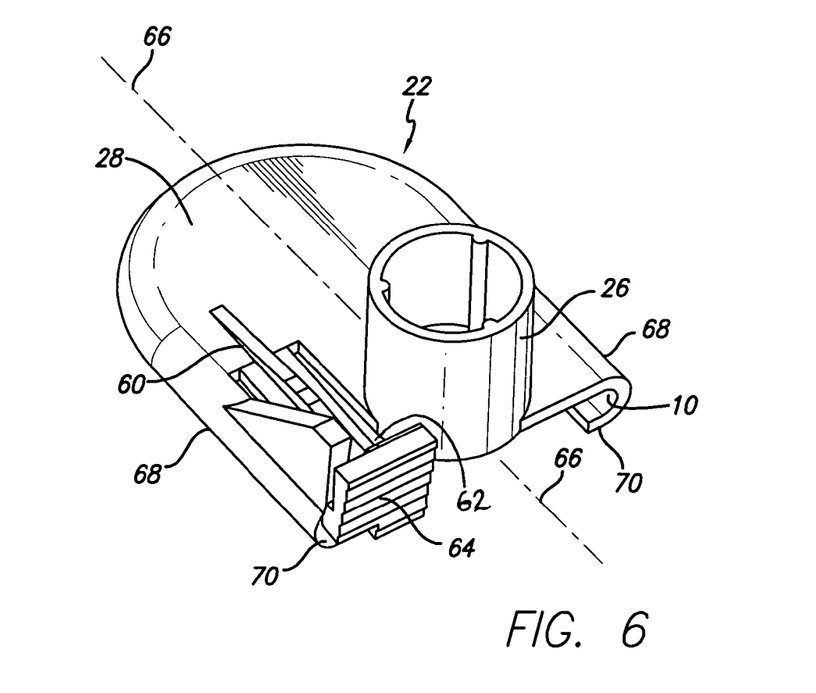
FIG. 6 is a top, left side perspective view of the base showing a locking arm, a release tab, and a tube aperture.

Turning now to the base, there is shown in FIG. 6 the base 22 with a flexible cantilevered locking arm 60 that is molded into the top surface 28 of the base, with its distal free end 62 biased downwardly below the top surface 28 of the base. Biasing of the free end downwardly is accomplished by molding the locking arm in a downwardly sloped configuration, but the biasing could also be accomplished by the use of springs or other means. A release tab 64 is formed on the locking arm 60, projecting upwardly from the locking arm in the general direction of the tower 26. It will be noted that the release tab 64 is located at a position sideways to the tower 26. The release tab is also offset from the longitudinal centerline 66 of the base. The free end 62 of the locking arm 60 can be flexed upwardly by pressing the release tab 64 in a direction parallel to the centerline 66. Without departing from the spirit of the invention, multiple locking arms and tabs offset from the centerline of the base may be used in place of the ones shown.

It should also be noted that the depth of the detent 48 and the size and angle of the locking arm 60 are carefully selected so that when the locking arm is located in the detent, it is unstressed. That is, it does not touch the bottom 69 (FIG. 5) of the detent with any significant force. This is important in that if the locking arm is formed of plastic material or other material that exhibits "creep," it may change shape if it is exposed to constant stress for an extended period. For example, if the clamp apparatus were stored in the occluding position (FIG. 1) for an extended period where the locking arm was in contact with the bottom of a shallower detent and was under continual stress due to constant contact with the detent, the locking arm may creep to where that storage position is the new at rest position of the locking arm. The locking arm would then become less effective. Thus, forming the detent and locking arm as described above so that the arm is unstressed will result in a clamp apparatus that is unaffected by storage. Similarly, the ramp is also of a depth that leaves the locking arm unstressed when at the lowest point of the ramp, as is the case in the open position shown in FIG. 12.

Figure 7:
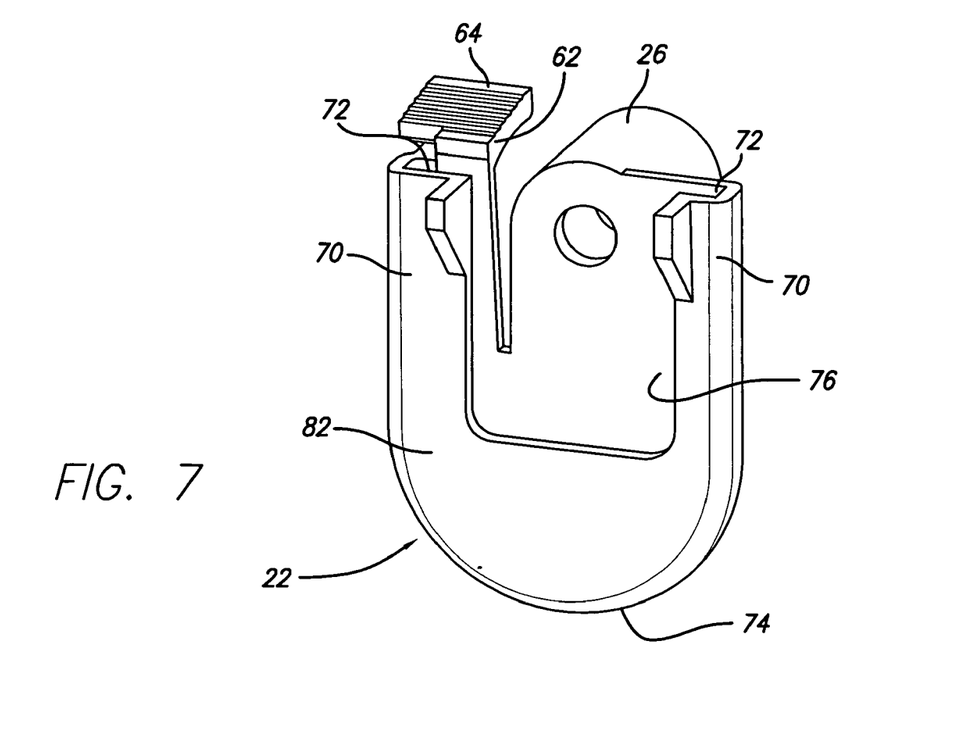
FIG. 7 is a bottom, right side perspective view of the base showing the locking arm and release tab.

The base also includes its side edges 68 formed into rails 70 that lie parallel to the direction of the relative sliding movement of the slide clamp in the base (FIG. 1). When the slide clamp 24 is slidingly engaged with the base 22, the slide clamp fits in a sliding fashion through the two rail channels 72 in the base. Alignment of the slide clamp with the base is accomplished by the fit of the slide clamp into the rail channels. Turning now to FIG. 7, the rails 70 and channels 72 can be seen more clearly. Additionally, it will be noted that the entire proximal end 74 of the base is enclosed. The center section 76 has been left open to accommodate the pulling projections of the slide clamp, as previously shown. Also more clearly seen is the distal free end 62 of the locking arm, as well as the releasing tab 64.

Figure 8:
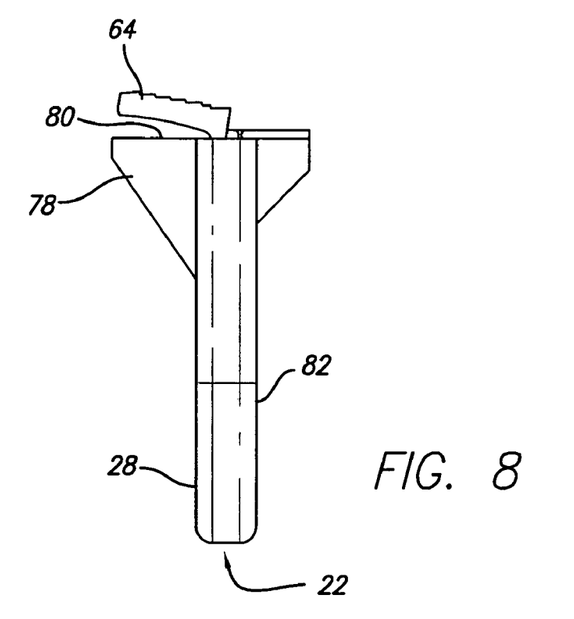
FIG. 8 is a right side plan view of the base showing the release tab.
Figure 9:
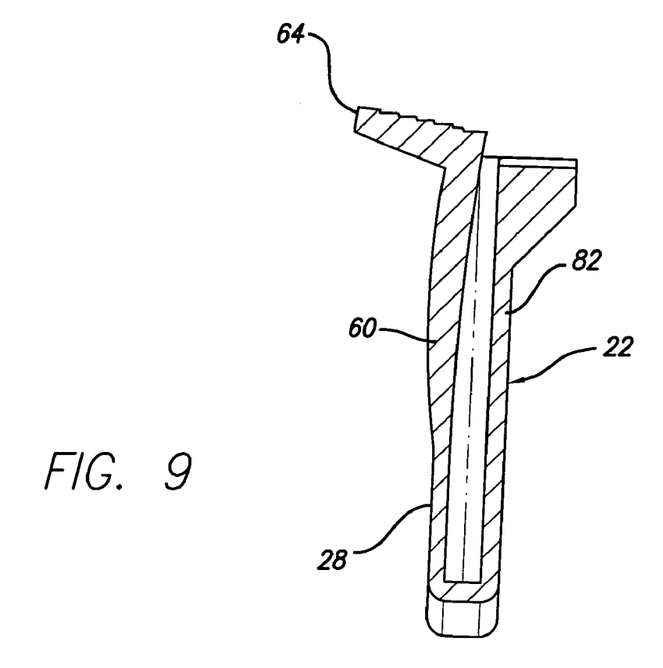
FIG. 9 is a cross-section left side view of the base showing the locking arm and release tab.

FIG. 8 shows a stop 78 formed on the top surface 28 of the base 22 that limits the range of movement of the release tab 64. In particular, a stop surface 80 is spaced away from the back of the releasing tab by a preselected distance so that the tab cannot be overstressed by bending it too far. Referring also to FIG. 9, a cross-section of the locking arm 60 with releasing tab 64 formed at its end is shown. It will be noted that the locking arm is molded as part of the base and is in a cantilever form. The releasing tab 64 is disposed at approximately ninety degrees to the locking arm but because the locking arm is formed at an angle to the upper 28 and the lower 82 surfaces of the base 22 so as to engage the slide clamp, the ninety degree angle of the releasing tab with the locking arm is other than ninety degrees to the top surface of the base. FIG. 9 more clearly illustrates the downward slope of the locking arm 60 to create the necessary downward bias to engage the detent 48 and locking edge 50 of the slide clamp to prevent the slide clamp from being moved to its open position until the locking arm 60 is moved out of the detent by intended action of the operator.

Figure 10:
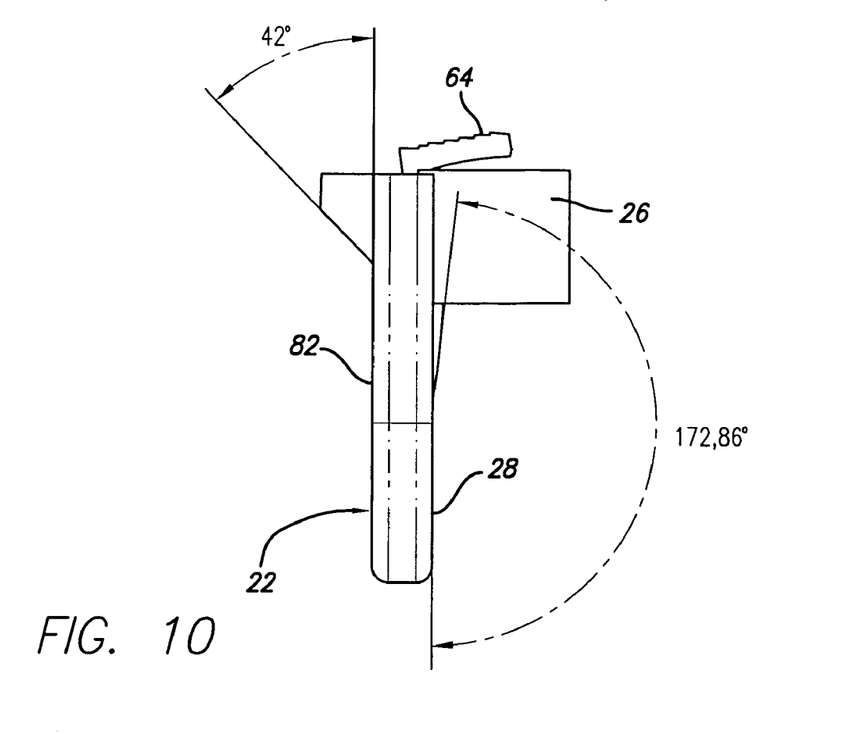
FIG. 10 is a left side view of the base showing the tube aperture, the release tab, and a portion of the locking arm, also shown in the angle of the locking arm with the upper base surface.
Figure 11:
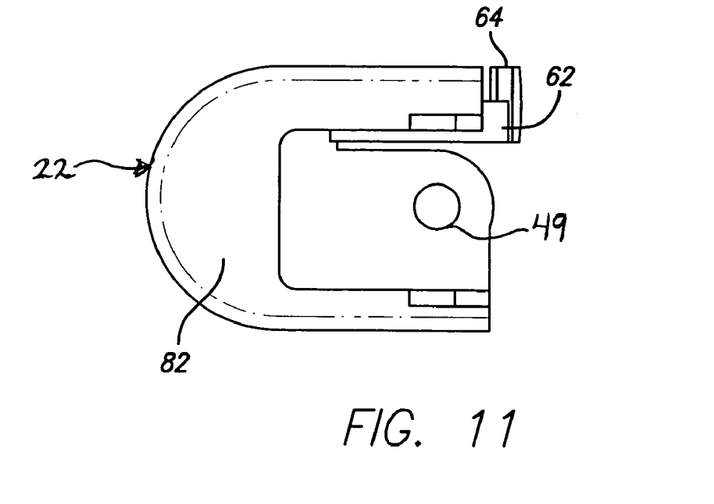
FIG. 11 is a bottom view of the base.

Referring now to FIG. 10, a right side view of the base is provided. It will be seen that the angle of the top surface of the locking arm is approximately 172.86 degrees relative to the top surface 28 of the base. This is also seen in FIG. 9. It has been found that thickening the locking arm and providing the angles shown results in repeatable performance. That is, when a releasing boss 90 (shown in FIG. 13) presses against the releasing tab 64, the tab and locking arm will rise away from the base and therefore away from the mounted slide clamp thus releasing the slide clamp for movement to the open position. This is discussed below in more detail. FIG. 11 presents a bottom view of the base 22 showing more clearly the distal end 62 of the locking arm that is received by the detent 48 of the slide clamp 24. Further, FIG. 11 shows the aperture 49 through the base for the tube.

Figure 12:
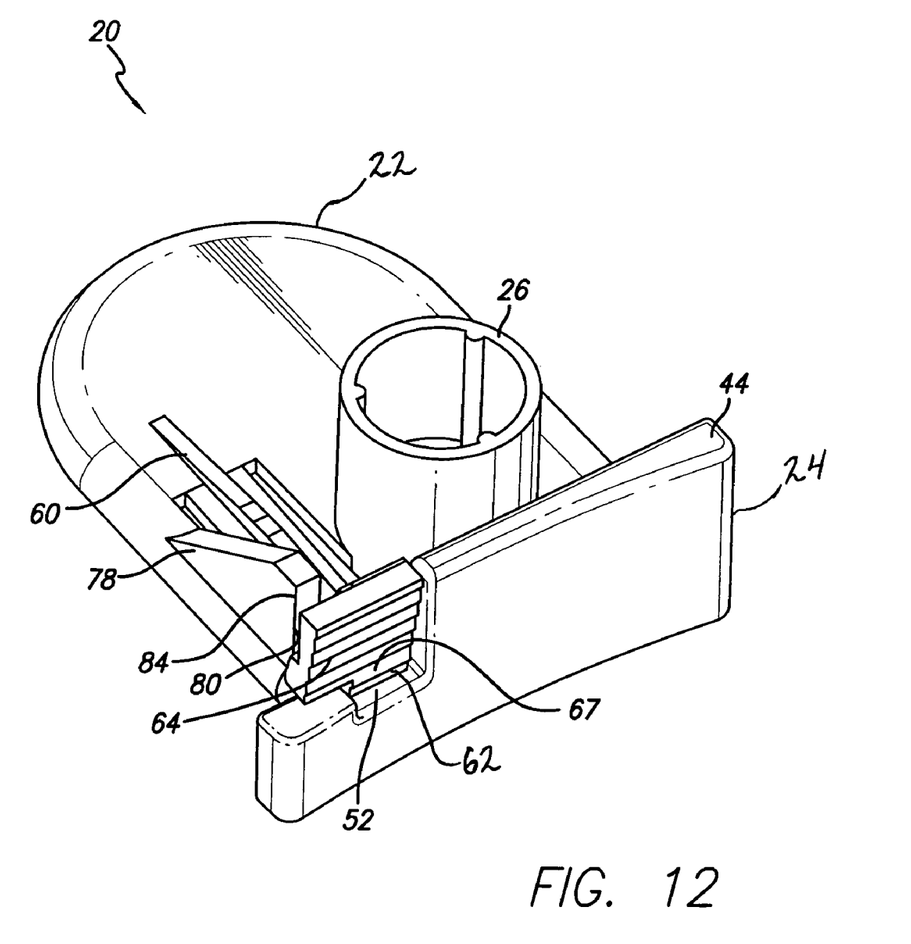
FIG. 12 is a top, left side perspective view of the automatic clamp apparatus of FIG. 1 in which the slide clamp has been inserted fully into the base resulting in the flow configuration.

FIG. 12 shows the assembled slide clamp 24 and base 22 into an operational automatic clamp apparatus 20 in accordance with aspects of the invention. Further, the clamp apparatus 20 is in the open position during which fluid may flow through the clamp apparatus. It will be seen that the distal free end 62 of the locking arm 60 resides in the ramp area 52, but the ramp is formed to be deep enough so that the distal free end 62 of the locking arm is not touching the material of the base and therefore, the locking arm is in an unstressed condition. In this configuration, the clamp apparatus 20 is in its smallest form thereby fitting into a pump with a closed door.

Figure 13:
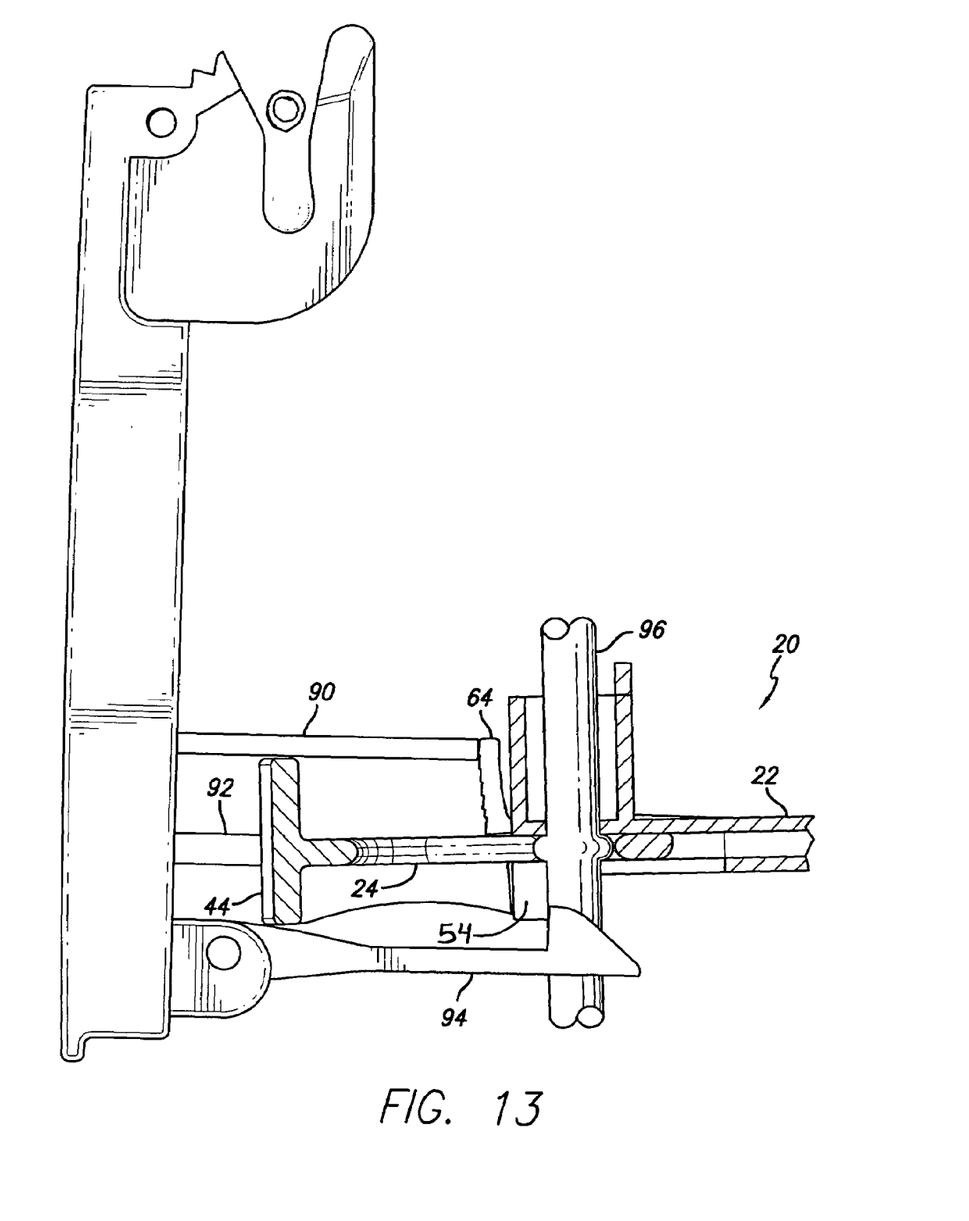
FIG. 13 is an operational view in which the tube is occluded by the aperture of the slide clamp, but a release boss and a pushing boss are about to move the slide clamp to the open or flow position.
Figure 14:
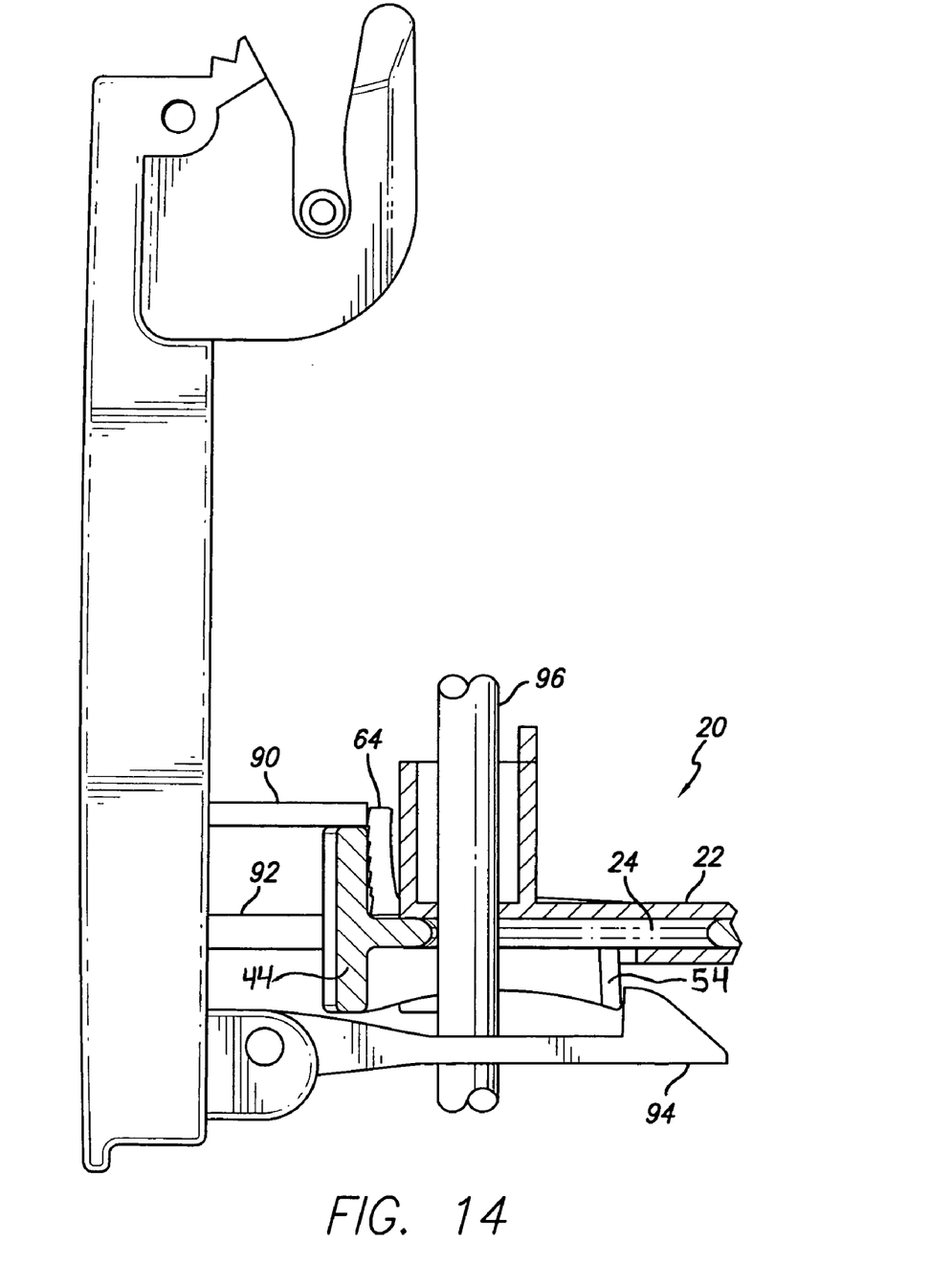
FIG. 14 is an operational view in which the tube is unoccluded for flow and a pulling hook is about to pull the slide clamp to the occluding position.

FIGS. 13 and 14 show in general how the automatic clamp apparatus 20 in accordance with aspects of the invention interacts with the door of a pump housing. FIG. 13 shows the slide clamp 24 in its occluding position relative to the base 22, with the slide clamp partially withdrawn from the base and the distal free end 62 of the locking arm 60 engaging the locking detent 48 (not shown) to hold the slide clamp in its occluding position. FIG. 14 shows the slide clamp in its open position with the slide clamp fully inserted within the base and the distal free end 62 of the locking arm flexed upwardly a sufficient amount to clear the detent 48.

Operative elements of the door and latch mechanism are shown schematically and designated as elements 90, 92, and 94, to illustrate their interaction with the automatic clamp apparatus of the present invention. A releasing boss 90 can be formed on the door and positioned to contact the release tab 64 as the door is moved to the closed position, and to press the release tab up and back. A pushing boss 92 can be formed on the latch mechanism and positioned to contact the pushing flange 44 on the slide clamp 24 as the latch is engaged to push the slide clamp from its occluding position (FIG. 13) to its open position (FIG. 14). Finally, one or more pulling hooks 94 can be formed on the latch mechanism and positioned to contact the pulling projections 54 as the latch is disengaged to pull the slide clamp 24 from its open position to its occluding position.

The releasing boss 90 and the pushing boss 92 of the door move generally to the right direction as seen in FIG. 13 when the door of the pump is moved to the closed position. The pulling hook 94 of the latch mechanism can be made to move generally to the left as seen in FIG. 14 when the latch is being disengaged, and to the right when the latch is being engaged, it being understood that other elements (not shown) of the latch mechanism perform the actual latching of the door in the shut position. In addition, the pulling hook 94 can rotate in the clockwise direction from the position shown, relative to the remainder of the latch mechanism, against a spring bias. For convenience, the conduit through the automatic clamp apparatus 20 is shown as a tube 96 in FIG. 13 and 14. In FIG. 13, the tube 96 is occluded by the slide clamp aperture and is spread into the occluding slot of that aperture. In FIG. 14, the tube is in the flow configuration. As mentioned above, a tube may or may not be used as the conduit through the clamp apparatus 20. A tower may be used with parts of tube formed to the tower.

Figure 15:
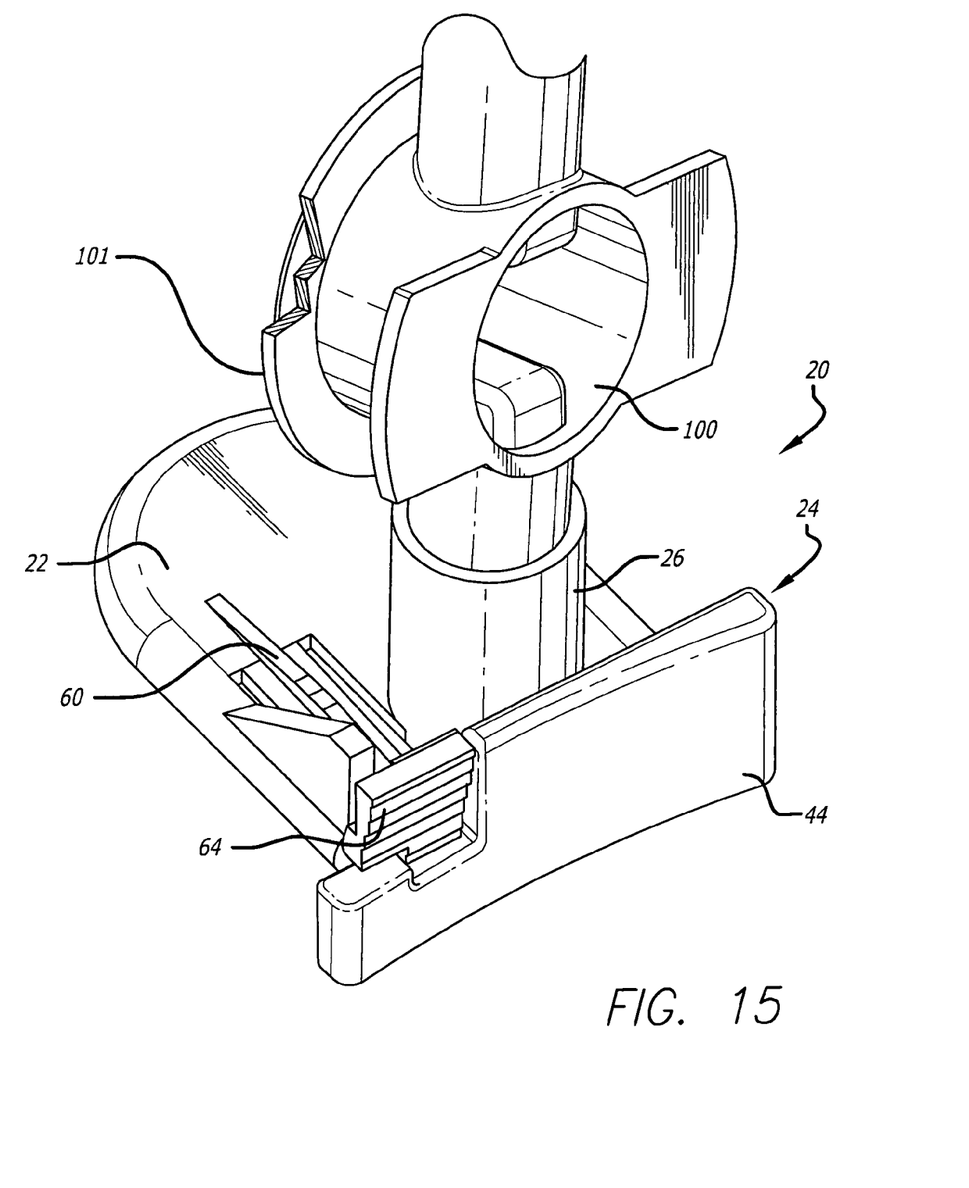
FIG. 15 is a view of the clamp apparatus having a pressure interface device located as part of the tube upstream from the clamp for communicating the line pressure to a pressure sensor.

Referring briefly to FIG. 15, the inclusion of a pressure interface device 100 upstream of the automatic clamp apparatus 20 is shown. This pressure interface device may take the form of a pressure diaphragm 101 having a size and configuration to be mounted to a pressure sensor that is a part of the infusion pump to which the clamp apparatus is to be mounted. Such a pressure diaphragm device is shown in U.S. Pat. No. 4,398,542 to Cunningham, and incorporated herein by reference. A sensor usable with such a pressure diaphragm is shown in U.S. Pat. No. 4,404,440 to Busche, also incorporated herein by reference. Mounting such a pressure diaphragm in line with the automatic clamp apparatus of the invention would restrict movement of the clamp apparatus along the line since it will need to be adjacent the pressure diaphragm to be fitted into the pump. In such a case, the tower 26 may be used as a mount for the pressure diaphragm device.

Operation

To use the automatic clamp apparatus 20 of the present invention, the slide clamp 24 is assured to be in the occluded position, as shown in FIG. 1. Because the locking arm 60 is located in the detent 48, the slide clamp cannot be moved from the occluding position to the open position unless the release tab 64 is actuated. While in the detent, the locking arm is unstressed. The upstream end of the IV tube 96 is connected to a fluid supply (not shown) of the chosen fluid to be pumped. The administration set containing the automatic clamp apparatus of the invention may be primed if necessary by the operator pressing a digit against the release tab to move it and the locking arm upwards out of the detent and another digit against the pushing flange to move the slide clamp to the open position. As the slide clamp is inserted into the base, the locking arm moves down the ramp 52 to the bottom of the ramp (FIG. 12) where it is unstressed. Priming may now occur. Once primed, the pushing flange is grasped by the operator and withdrawn from the base to restore the slide clamp to the occlusion position as shown in FIG. 1 so that the free flow of fluid through the IV tube cannot occur.

The door of the pump housing is opened and the automatic clamp apparatus 20 and tubing above and below the clamp apparatus 20 are installed into the pump appropriately. The pushing flange is used by the operator to receive a digit of the operator for pushing the clamp apparatus into the appropriate cavity of the pump. The clamp apparatus should remain in the occlusion configuration during this installation into the pump. Because the release tab is off center in relation to the pushing flange, the chances of the operator pressing it instead or with, the pushing flange are greatly reduced.

The upstream and downstream tubing is now engaged with any other devices that exist, such as an air-in-line sensor, pressure sensors, etc. Especially, the pumping tube 96 is placed in contact with the pumping mechanism, and the door of the pump is then shut. FIG. 13 shows the slide clamp 24 in its occluding position, with the release boss 90 about to contact the release tab 64 as the door of the pump is shut. As the door is completely shut, the release boss 90 presses the release tab 64 upward thereby flexing the locking arm 60 upward and out of the detent 48 thereby permitting movement of the slide clamp so that it can be inserted into the base. After the door is completely shut, the latching mechanism is latched, causing the pushing boss 92 to push the slide clamp 24 and insert it into the base to its open position as shown in FIG. 12. FIG. 14 shows the slide clamp 24 in its open position, with the pulling hook 94 having pivoted behind the pulling projection 54. The pump can then be operated in the conventional fashion to purge the IV tube 96 of air, and the IV tube 96 can be connected to a venous access site.

When the pump door is to be opened, the boss 92 and the hook 94 will be moved to the left, causing the pulling hooks 94 to contact the pulling projection 54 of the slide clamp 24 and withdraw the slide clamp 24 from the base to its occluding position. The latching mechanism can be constructed by known means so that only after this occlusion occurs will the door be unlatched. At this time, the door can be opened. The locking arm 60 having engaged the locking detent 48 maintains the slide clamp 24 in its occluding position, even if the slide clamp 24 is pushed toward the base 22 with considerable force.

The latching mechanism can also be constructed by known means so that when the door has been unlatched, the latching mechanism can not be moved back to its latched position until the door has been shut. Therefore, if the door is to be shut, the releasing boss 90 will press the release tab 64 upward to release the locking arm 60 from engagement with the detent 48, and the slide clamp 24 can be subsequently moved to the open position as explained before.

While the particular automatic clamp apparatus as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A clamp apparatus for selectively preventing fluid flow through a resilient tube, comprising:
    a base having a tube aperture at which the resilient tube may be located, the base having a longitudinal center line;
    a slide clamp slidably mountable on the base for movement between an occluding position and an open position, the slide clamp having a clamp top surface and a longitudinal center line;
    a clamp aperture formed in the slide clamp for receiving the tube therethrough;
    a constricted region formed in the clamp aperture, the constricted region occluding the tube to prevent fluid flow through the tube when the slide clamp is in the occluding position;
    an open region formed in the clamp aperture, the open region allowing fluid flow through the tube when the slide clamp is in the open position;
    a flexible cantilevered locking arm mounted on the base, the locking arm being biased toward the slide clamp at a selected angle from the base to a locking position at which the locking arm prevents movement of the slide clamp from the occluding position to the open position, the locking arm being deflectable to allow subsequent movement of the slide clamp from the occluding position to the open position; and
    a detent in the slide clamp defined by a detent edge and a bottom portion adjacent the detent edge, the bottom portion located at a depth below the clamp top surface, the depth accommodating the selected angle of the locking arm such that, when the slide clamp is in the occluding position, a portion of the locking arm is located in the detent so as to engage the detent edge while not touching the bottom portion of the detent, thereby preventing the slide clamp from moving from the occluding position and thereby keeping the locking arm unstressed.

2. The clamp apparatus of claim 1 wherein the tube aperture of the base slidably receives the resilient tube such that the base may be slid along the tube to a selected position when the slide clamp is in the open position.

3. The clamp apparatus of claim 1 wherein the locking arm further comprises a release tab for releasing the flexible arm from the slide clamp, to allow subsequent movement of the slide clamp from the occluding position to the open position.

4. The clamp apparatus of claim 3 wherein the base further comprises a stop surface located at a position adjacent the release tab to interfere with movement of the release tab beyond a preselected range of movement.

5. The clamp apparatus of claim 3 wherein the release tab is located at a position offset from the longitudinal center line of the base.

6. The clamp apparatus of claim 5 wherein the release tab is disposed for deflecting the flexible arm out of the detent to allow subsequent movement of the slide clamp from the occluding position to the open position.

7. The clamp apparatus of claim 1 wherein the slide clamp further comprises a ramp to receive the locking arm when the slide clamp is in the open position, the ramp formed to be deeper than the arm whereby the arm is unstressed when the slide clamp is in the flow position.

8. The clamp apparatus of claim 7 wherein the ramp is formed to guide the locking arm into the detent formed in the slide clamp as the slide clamp is being moved from the open position to the occluding position to thereby lock the slide clamp in the occluding position.

9. The clamp apparatus of claim 1 wherein:
    the aperture is approximately tear-drop shaped;
    the constricted region comprises an elongated slot portion;
    the flow region comprises a rounded portion;
    the tube is located in the slot portion when the slide clamp is in the occluding position; and
    the tube is located in the round portion when the slide clamp is in the open position.

10. The clamp apparatus of claim 1 wherein the tube aperture comprises a tower into which a tube end may be attached.

11. The clamp apparatus of claim 1 wherein the tube aperture comprises a fluid passageway through the base, whereby the resilient tube is connected in fluid communication with the passageway.

12. The clamp apparatus of claim 1 further comprising a pressure interface device located between the resilient tube and the base, the pressure interface device having a pressure diaphragm mounted in a housing, the pressure diaphragm formed to conduct pressure increases and decreases of the resilient tubing to a pressure sensor.

13. The clamp apparatus of claim 1 wherein the slide clamp further comprises a front pushing flange large enough to receive a digit of an operator used to push the clamp apparatus into position in a medical infusion pump, the pushing surface being concave.

14. The clamp apparatus of claim 13 wherein the release tab is located at a position other than behind the pushing flange.

15. The clamp apparatus of claim 14 the release tab is located at a sideways position in relation to the pushing flange.

16. The clamp apparatus of claim 1 wherein:
    the locking arm further comprises a release tab for releasing the flexible arm from the slide clamp, to allow subsequent movement of the slide clamp from the occluding position to the open position;

the base further comprises a stop surface located at a position adjacent the release tab to interfere with movement of the release tab beyond a preselected range of movement;

the slide clamp comprises a ramp to receive the locking arm when the slide clamp is in the open position, the ramp formed to be deeper than the locking arm whereby the locking arm is not under stress when the slide clamp is in the flow position, the ramp further formed to guide the locking arm into the detent as the slide clamp is being moved from the open position to the occluding position to thereby lock the slide clamp in the occluding position;

the slide clamp further comprises a front pushing flange large enough to receive a digit of an operator used to push the clamp apparatus into position in a medical device, the pushing surface being concave; and the release tab is located at a position other than behind the pushing flange.

17. The clamp apparatus of claim 16 wherein the release tab is located at a sideways position in relation to the pushing flange.

18. A clamp apparatus for selectively preventing fluid flow through a resilient tube, comprising:

a base having a tube aperture at which the resilient tube may be located, the base having a longitudinal center line;

a slide clamp slidably mountable on the base for movement between an occluding position and an open position, the slide clamp having a longitudinal center line;

a clamp aperture formed in the slide clamp for receiving the tube therethrough;

a constricted region formed in the clamp aperture, the constricted region occluding the tube to prevent fluid flow through the tube when the slide clamp is in the occluding position;

an open region formed in the clamp aperture, the open region allowing fluid flow through the tube when the slide clamp is in the open position;

a flexible cantilevered locking arm mounted on the base, the locking arm being biased toward a locking position to prevent movement of the slide clamp from the occluding position to the open position, the locking arm having a release tab located at a position offset from a longitudinal center line of the base for deflecting the locking arm from the locking position to allow movement of the slide clamp to the open position;

a detent in the slide clamp into which the locking arm is biased to the locking position and into which the locking arm is located when the slide clamp is in the occluding position to prevent the slide clamp from moving from the occluding position, the detent being large enough to receive the locking arm such that the locking arm is unstressed while in the detent;

a stop surface located on the base at a position adjacent the release tab to interfere with movement of the release tab beyond a preselected range of movement; and a ramp located on the base to receive the locking arm when the slide clamp is in the open position and to guide the locking arm into a detent formed in the slide clamp as the slide clamp is being moved from the open position to the occluding position to thereby lock the slide clamp in the occluding position, the ramp formed to be deeper than the arm whereby the locking arm is unstressed when the slide clamp is in the flow position.

19. The clamp apparatus of claim 18 wherein the slide clamp further comprises a front pushing flange large enough to receive a digit of an operator used to push the clamp apparatus into position in a medical infusion pump, the pushing surface being concave.

20. The clamp apparatus of claim 18 wherein the tube aperture comprises a tube sleeve within which a tube end may be permanently mounted.

* * * * *

UNITED STATES PATENT AND TRADEMARK OFFICE
CERTIFICATE OF CORRECTION

PATENT NO. : 7,124,996 B2  Page 1 of 1
APPLICATION NO. : 10/892941
DATED : October 24, 2006
INVENTOR(S) : Christopher J. Clarke and René Ruedi It is certified that error appears in the above-identified patent and that said Letters Patent is hereby corrected as shown below:

Sheet 2 of 10 of the Drawings, delete "FIG. 6" and insert instead the drawing below FIG. 6.

FIG. 6

Signed and Sealed this

Twelfth Day of June, 2007

JON W. DUDAS
*Director of the United States Patent and Trademark Office*